United States Patent [19]
Gabilly

[11] Patent Number: 6,083,442
[45] Date of Patent: Jul. 4, 2000

[54] PROCESS FOR TAKING IMPRESSIONS, PARTICULARLY OF THE HUMAN BODY, AND CORRESPONDING MATERIAL

[75] Inventor: Daniel Gabilly, Niort, France

[73] Assignee: Societe des Etablissements Hilaire Gabilly Orthopedie Podologie Niort, Niort, France

[21] Appl. No.: 08/868,671

[22] Filed: Jun. 4, 1997

[30] Foreign Application Priority Data

Jun. 4, 1996 [FR] France ................................. 96 07168

[51] Int. Cl.⁷ ............................. B29C 33/40; B28B 11/14
[52] U.S. Cl. ..................... 264/163; 264/222; 264/223; 264/DIG. 30; 425/2
[58] Field of Search ................................. 264/222, 223, 264/DIG. 30, 163; 425/2

[56] References Cited

U.S. PATENT DOCUMENTS

| | | | |
|---|---|---|---|
| 1,351,789 | 9/1920 | Rowley | 264/222 |
| 3,853,124 | 12/1974 | Larson | 128/90 |
| 3,895,405 | 7/1975 | Edwards | 12/146 M |
| 4,006,542 | 2/1977 | Larson | 36/43 |
| 4,019,505 | 4/1977 | Wartman | 128/90 |
| 4,932,852 | 6/1990 | Suzuki | 425/2 |
| 5,015,429 | 5/1991 | Suzuki | 264/138 |
| 5,415,623 | 5/1995 | Cherubini | 602/7 |

FOREIGN PATENT DOCUMENTS

| | | |
|---|---|---|
| 0 323 099 | 7/1989 | European Pat. Off. . |
| 4 224 827 | 1/1994 | Germany . |
| WO 90/05504 | 5/1990 | WIPO . |

*Primary Examiner*—Jan H Silbaugh
*Assistant Examiner*—Suzanne E. Mason
*Attorney, Agent, or Firm*—Young & Thompson

[57] ABSTRACT

An impression of a portion of a human body is made by forming a preform of standard profile of polymeric material with shape memory that is substantially rigid at ambient temperature and flexible and elastic at a higher working temperature, bringing the preform to that working temperature, and placing the preform on that body portion. After cooling of the preform to below the working temperature, the preform is removed from the body portion and a positive model is cast from the preform. The preform is then returned to the working temperature without physical constraint, whereupon the preform resumes its standard profile and so can be re-used a number of times. The polymeric composition comprises at least one elastomer and one polycaprolactone diluted in a composition of solvents that dissolve the polymers. The elastomer is polyurethane. The composition of solvents comprises dimethyl-formamide to dissolve the polyurethane, toluene to dissolve the polycaprolactone, and methylethylketone as a buffer.

1 Claim, No Drawings

PROCESS FOR TAKING IMPRESSIONS, PARTICULARLY OF THE HUMAN BODY, AND CORRESPONDING MATERIAL

This application corresponds to French application 96 07168 of Jun. 4, 1996, the disclosure of which is incorporated herein by reference.

The present invention relates to a process for taking impressions for producing products adapted to the shape of a portion of a person's anatomy, particularly for the production of orthopaedic shoes. The invention also relates to material permitting the practice of this process.

Podo-orthesists, for example, produce shoes permitting persons having deformed or withered or mutilated feet, to have walking shoes.

The first step consists in taking the imprint of the foot of the person. This step is at present carried out with plaster strips. These strips are wound about the foot after having been moistened to activate the plaster.

There are drawbacks connected with the emplacement of these strips, both from the point of view of handling which requires a certain manual skill, as well as the point of view of comfort of the person whose foot and clothing must be protected from possible splattering of plaster.

Even if the time consumed is reduced, it must not be too great because the emplacement of the strips requires a certain time and it is not possible to slow the setting of the plaster in the course of emplacement, which requires the provision of a safety margin which substantially increases the time of setting of a plaster cast.

This cast is a female replica and the male impression is produced for producing a first trial of the shoe.

Once the drying time for the strip has passed, it is cut off to be withdrawn from the foot of the person.

Polyurethane is then cast into the mold to provide a positive model, and this rough model is finished by machining and corrected. The corrected shape, which thus has an entirely suitable surface, permits the technician to produce the shoe.

This method is costly in material, but the operating time is greater and it also leads to the disagreeable results mentioned above.

It would be interesting to have a process using a material which ensures taking a sharp impression and which permits repeating this several times.

The object would be to be able to adjust optimally the configuration of the material to the foot of the person and hence to be able to take again the imprint almost instantaneously if that is necessary.

The object of the present invention is to provide a process for taking impressions of a portion of the anatomy of a human being, particularly a foot for the provision of orthopaedic shoes, which are characterized in that it comprises the following steps:

making a preform of a standard profile in polymeric material with shape memory, substantially rigid at ambient temperature and flexible and elastic at its working temperature, in either case the temperature being tolerable by the human skin, raising the temperature of the preform to the working temperature, fitting the preform about the part in question, waiting for cooling of the preform to below its working temperature, retracting the preform from the portion in question and casting the positive shape, and returning the preform to its initial standard shape by raising its temperature to its working temperature without constraint of the preform, so as to be able to reuse the preform for taking another impression.

More particularly, the preform is brought to the working temperature by passage through a hot water bath or through a hot air oven.

The invention also relates to the making of the preform which comprises the following steps:

immersing in a bath or spray a preform of standard shape with a composition of polymers having shape memory diluted in a solvent, evaporating the solvent, and cutting away the polymeric preform according to lines adapted to permit its opening, and securing to the preform quick closure means.

The polymeric composition for making a preform useful in the process comprises at least one elastomer and one polycaprolactone diluted in a composition of solvents suitable for dissolving at least one and the other of the polymers.

More particularly, the elastomer is polyurethane.

As to the composition of the solvents, they comprise dimethylformamide to dissolve the polyurethane, toluene to dissolve the polycaprolactone, and methylethylketone as a buffer.

The invention is described hereafter according to a particular non-limiting example.

There should first of all be produced a preform of a polymeric material having shape memory. These preforms are made from templates, if desired of special sizes without it being necessary to spend important sums for the production of these templates. These templates are generally made as a function of known size graduations to permit adaptation to each of the sizes or a series of sizes of the range of non-orthopaedic shoes, but often beyond that range to take account of extreme cases. There can thus be provided a range of preforms according to a particular scale.

These preforms are made by immersing the templates in baths of polymer with shape memory, diluted in a solvent, or by spraying of this polymer with shape memory.

Once the solvent has evaporated, the polymeric shell is cut away so as to be able to permit its withdrawal.

In line with these cuts, there should be integrated closure means such as quick closure strips of hook-and-eye material. This integration can be carried out after but preferably at the same time as for example the spraying or other coating of the template.

There is thus obtained a preform having a substantially standard profile, with sizes varying as a function of the usual range of sizes.

When the podo—orthesist desires to take an imprint of the foot of a person, he chooses from among the preforms that which most closely approaches the foot in question and performs a further step of the process according to the invention.

He raises the temperature of the preform to a temperature suitable for its deformation. He opens the closure means to permit fitting the preform like a boot on the foot and then the closure means are closed.

The temperature of the preform is of course bearable by the skin of the patient. For example, the preform can be heated solely by immersing it in a bath at 60° C. or better still in a hot air oven thermostatically controlled, which avoids handling water thereby avoiding the risk of staining or splashing in the vicinity of the operation, as was the case with plaster.

The preform thus being emplaced, is deformed manually if necessary, in addition to its own elasticity, to ensure that it matches well the contour of the foot and particularly the part of the foot which gives rise to the problem.

Very quickly, the cooling of the preform gives rise to sufficient rigidification so that it is possible to withdraw this preform by opening the closure means.

If the impression is not satisfactory, the same preform is again raised to its working temperature and then the operation repeated, which requires only several seconds.

If the impression is satisfactory, a positive shape is cast in polyurethane, but in this case, machining and correction are not needed because the surface condition of the preform is such that it gives a positive shape directly usable for production of the shoe.

The polymerization reaction of the polyurethane is only slightly exothermic so that the preform faithfully keeps the impression.

The preform, once the shoes has been produced, is returned to its original profile by raising its temperature. In the absence of forced deformation by the introduction of a solid element into its interior, the preform returns to the original profile it had after evaporation of the solvents, which is to say that of the template, thanks to its shape memory.

More particularly, a material usable for practicing this process is a composition of an elastomer and a polycaprolactone.

Thus, the elastomer ensures the elastic effect to match the contours and the polycaprolactone ensures the effect of rigidification and blocking the deformation of the elastomer at ambient temperature with sufficient softening for a small temperature elevation.

A material which is satisfactory for producing such preforms comprises two polymers in a composition of solvents.

The first polymer is polyurethane and the second polymer is polycaprolactone.

The composition of solvents comprises three solvents: dimethylformamide, methylethylketone, and toluene, serving respectively as solvent for the polyurethane, buffer, and solvent for the polycaprolactone.

Thus it is necessary to avoid bubbles during evaporation of the solvent, segregation and other parasitic effects whilst ensuring rapid evaporation of the solvents.

According to a further advantage of the invention, there can be integrated into the preform temperature indication means by pigments sensitive to heat and whose color varies as a function of the temperature, such that for a given color, one knows that the temperature of the preform is at the softening temperature sufficient for taking an imprint or on the contrary that the preform is at the rigidification temperature permitting its removal.

There can also be envisaged providing information elements such as sizes for example within the thickness of the preform and also germicidal and fungicidal elements to ensure permanent treatment of the preform.

According to other desirable features of the invention, there can also be provided a supplemental internal layer to avoid the preform sticking tightly to the skin during fitting.

A treatment by radiation can also permit the decrease of this property of sticking, whilst increasing the elastic capabilities of the preform when it is brought to its working temperature.

All the description has been given with respect to an orthopaedic product so as to give all the details of the process according to the invention, but this embodiment must not be considered limitative.

Thus, such a material is itself adapted to find important applications in medical fields such as post-traumatic support, surgical, or orthotic compression devices for burns.

For physical therapy, there can be produced suitable splints.

What is claimed is:

1. A process for production of a positive model of orthopaedic equipment, using a preform with a shape memory material, comprising the steps of:

coating a template with a composition of polymers with shape memory dissolution comprising at least one solvent and that is substantially rigid at an ambient temperature and flexible and elastic at a working temperature that is higher than the ambient temperature;

evaporating the at least one solvent from the coated template to produce the preform from the composition of polymers;

cutting away the polymeric preform according to lines which permit withdrawal of the preform from the template;

withdrawing the preform from the template;

heating the preform to the working temperature;

placing the preform on a human foot;

cooling the preform to below the working temperature to form an impression of the foot in the preform;

removing the impressed preform from the foot;

closing the impressed preform;

casting a positive model in the impressed preform;

opening the impressed preform and withdrawing the positive model from the impressed preform; and returning the impressed preform to the working temperature without physical constraint, whereby the impressed preform resumes a shape of the preform before the preform was first heated to the working temperature.

* * * * *